(12) United States Patent
Myung

(10) Patent No.: US 12,133,808 B2
(45) Date of Patent: Nov. 5, 2024

(54) BILIARY STENT UNIT

(71) Applicant: BCM Co., Ltd., Gyeonggi-do (KR)

(72) Inventor: Byung Cheol Myung, Gyeonggi-do (KR)

(73) Assignee: BCM CO., LTD., Gyeonggi-do (KR)

( * ) Notice: Subject to any disclaimer, the term of this patent is extended or adjusted under 35 U.S.C. 154(b) by 517 days.

(21) Appl. No.: 17/477,212

(22) Filed: Sep. 16, 2021

(65) Prior Publication Data

US 2022/0087842 A1    Mar. 24, 2022

(30) Foreign Application Priority Data

Sep. 24, 2020 (KR) .......................... 10-2020-0124140

(51) Int. Cl.
*A61F 2/95* (2013.01)
*A61F 2/04* (2013.01)

(52) U.S. Cl.
CPC .............. *A61F 2/9522* (2020.05); *A61F 2/04* (2013.01); *A61F 2002/041* (2013.01); *A61F 2002/9511* (2013.01); *A61F 2210/0014* (2013.01)

(58) Field of Classification Search
CPC ................ A61F 2/95; A61F 2002/9511; A61F 2002/9528; A61F 2002/9534; A61F 2/9522; A61F 2002/041; A61F 2/04; A61F 2210/0014; A61F 2250/0059; A61F 2/07; A61F 2/962; A61F 2002/8486; A61F 2220/0008; A61F 2/90; A61F 2/848; A61L 31/022; A61L 31/04; A61L 2400/16
See application file for complete search history.

(56) References Cited

FOREIGN PATENT DOCUMENTS

KR    20100127529    *    5/2009    ............... A61F 2/04

OTHER PUBLICATIONS

KR20100127529 Translation (Year: 2010).*

* cited by examiner

*Primary Examiner* — Brian A Dukert
*Assistant Examiner* — Rebecca Lynee Zimmerman
(74) *Attorney, Agent, or Firm* — IP & T GROUP LLP

(57) ABSTRACT

Proposed is a biliary stent unit having a pulling string that is fixed to the skin of a human body to prevent a stent from separating from a diseased part of the biliary tract, and having a soft tube that reduces stimulus in the human body after a surgery because it has flexibility.

8 Claims, 15 Drawing Sheets

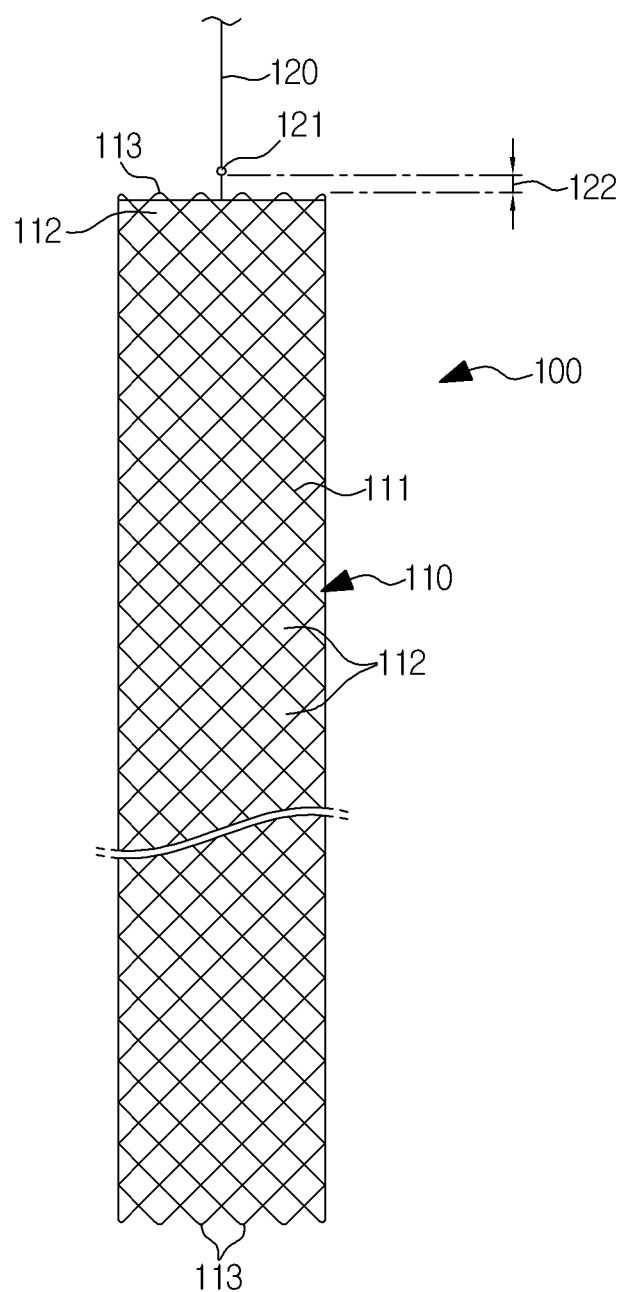
[FIG. 1]

[FIG. 2]
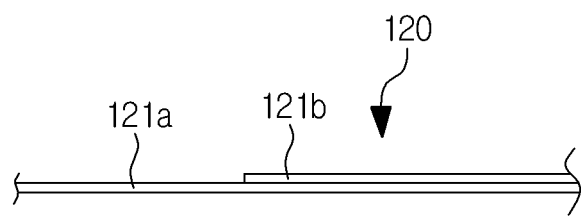
[FIG. 3]
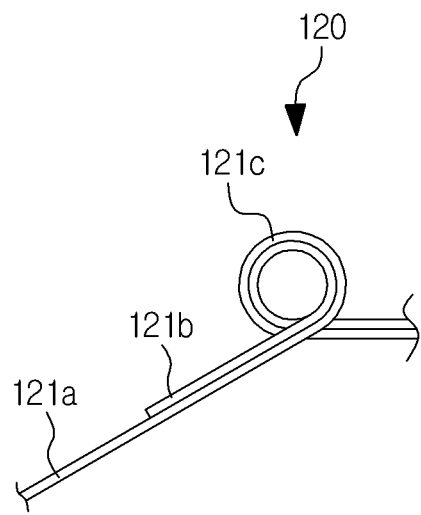

[FIG. 4]
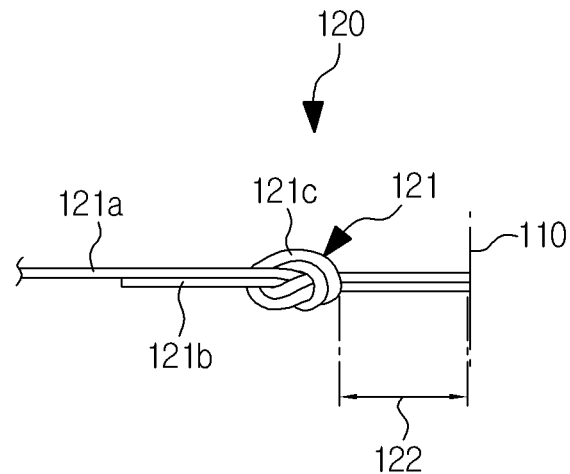
[FIG. 5]
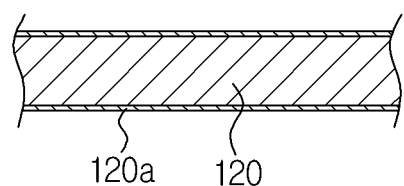
[FIG. 6]
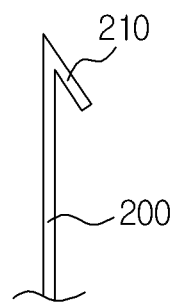

[FIG. 7]
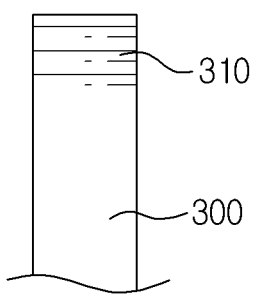
[FIG. 8]
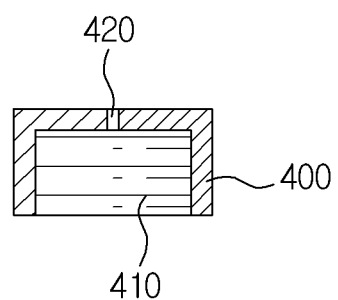

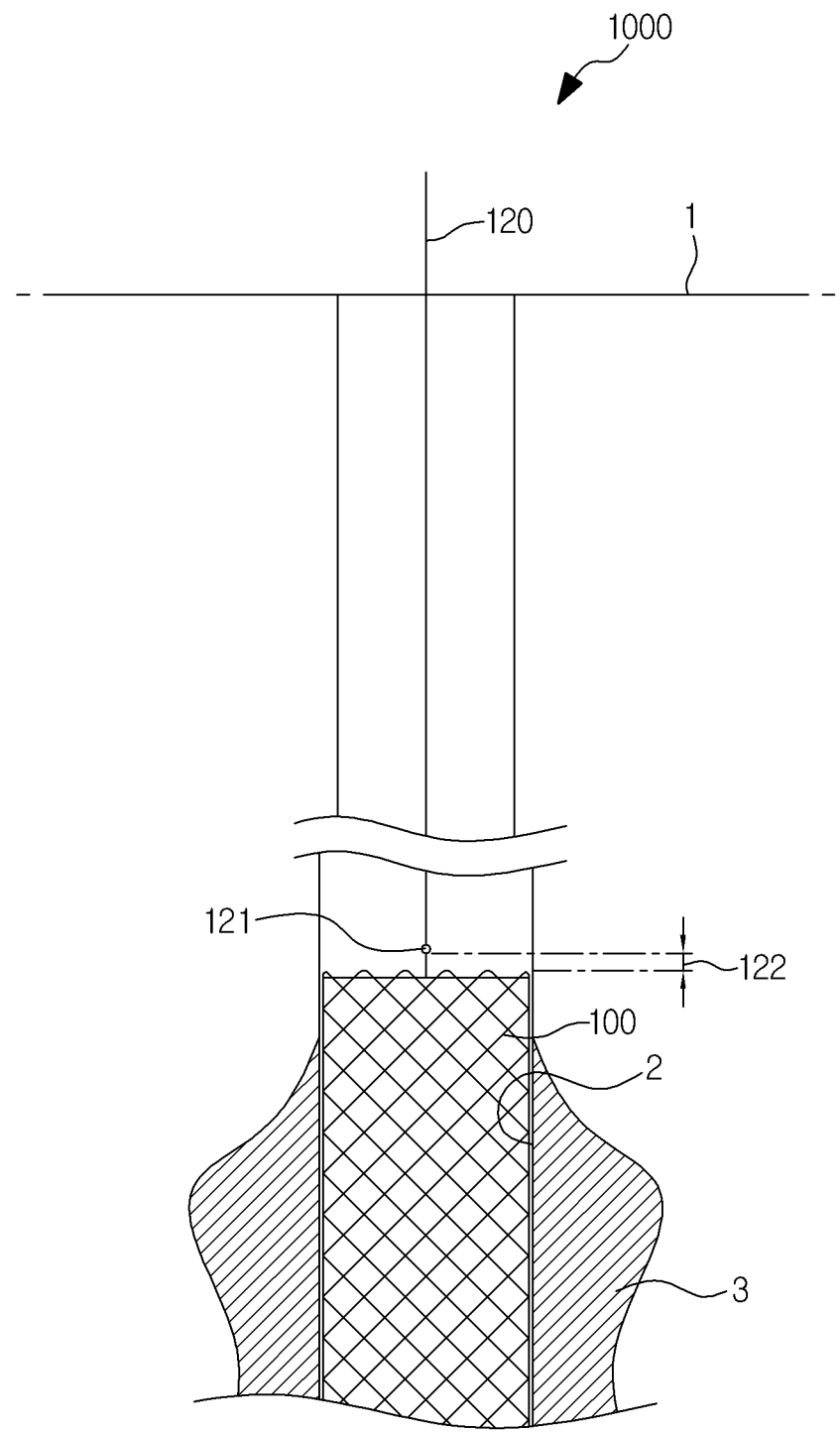

[FIG. 10]
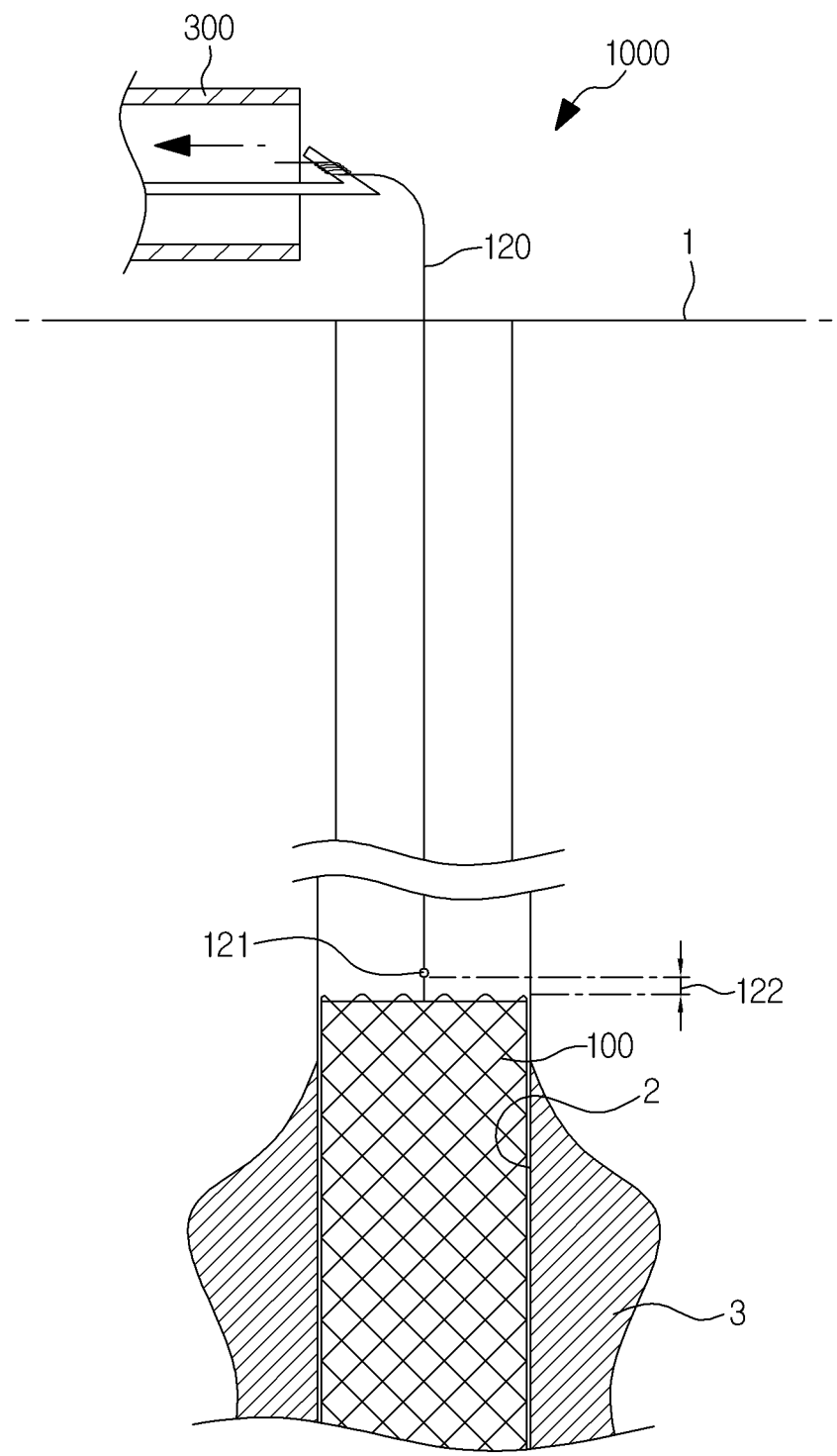

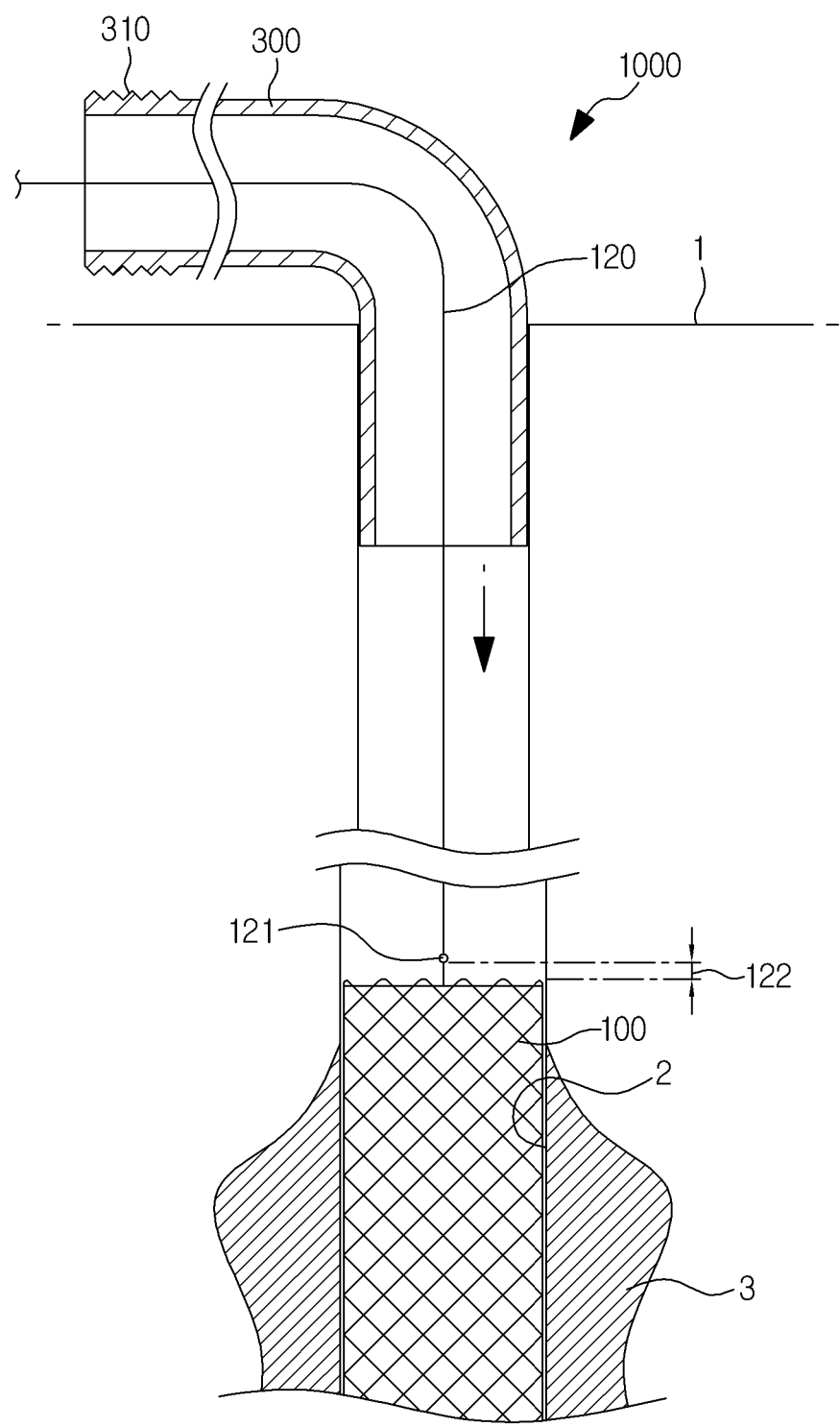
[FIG. 11]

[FIG. 12]
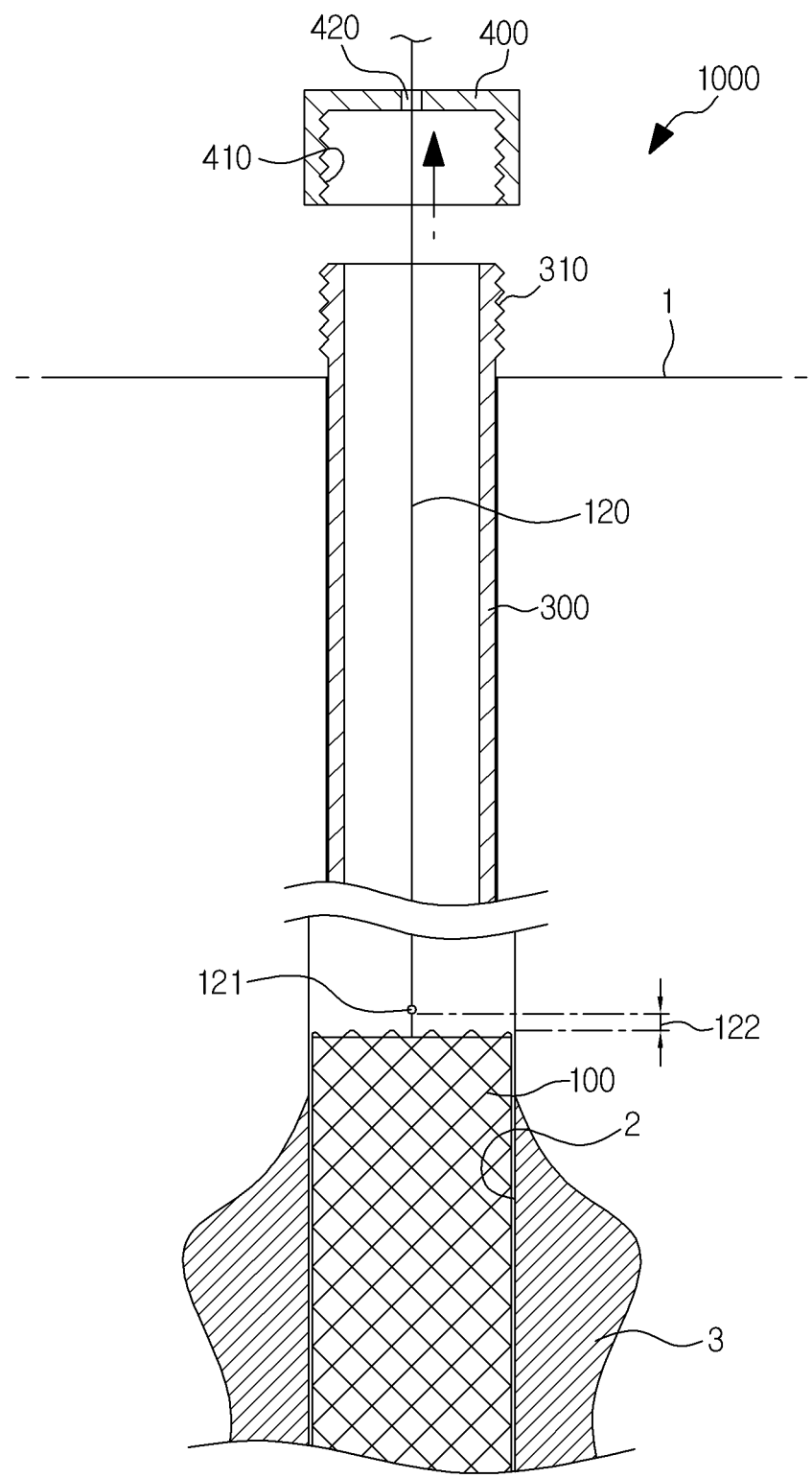

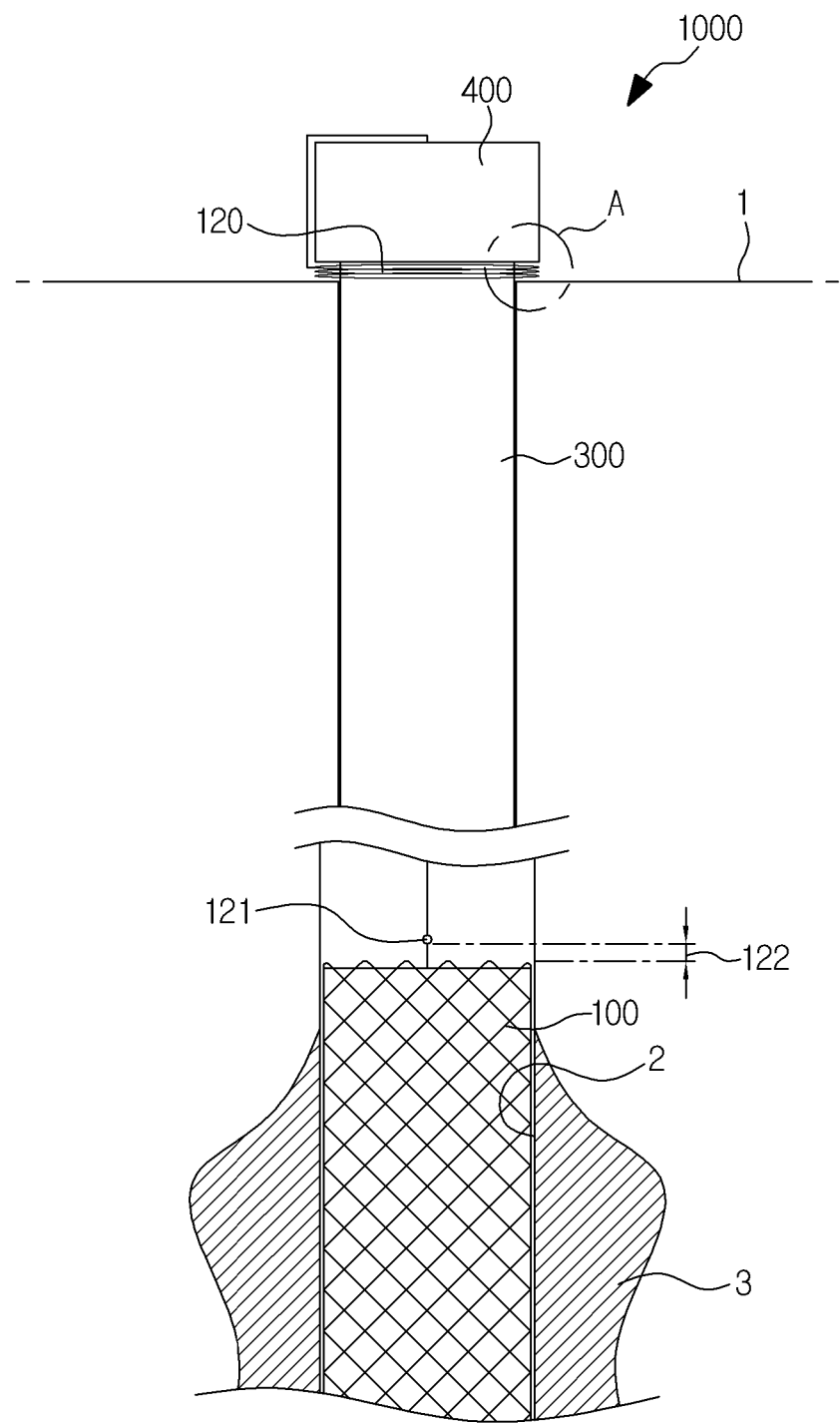
[FIG. 13]

[FIG. 14]
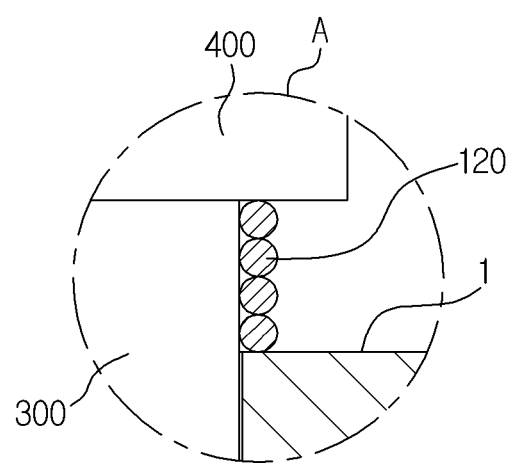

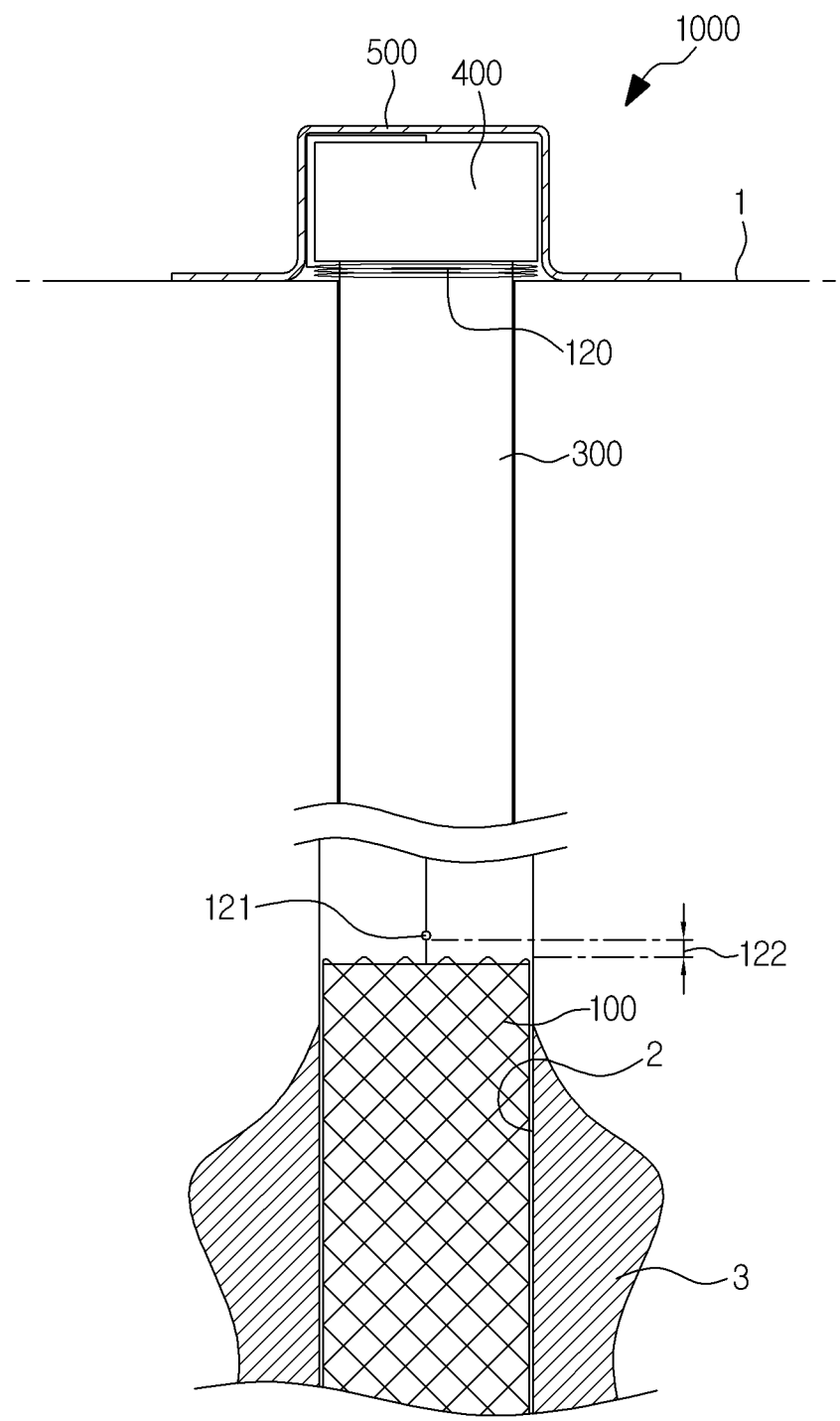
[FIG. 15]

[FIG. 16]
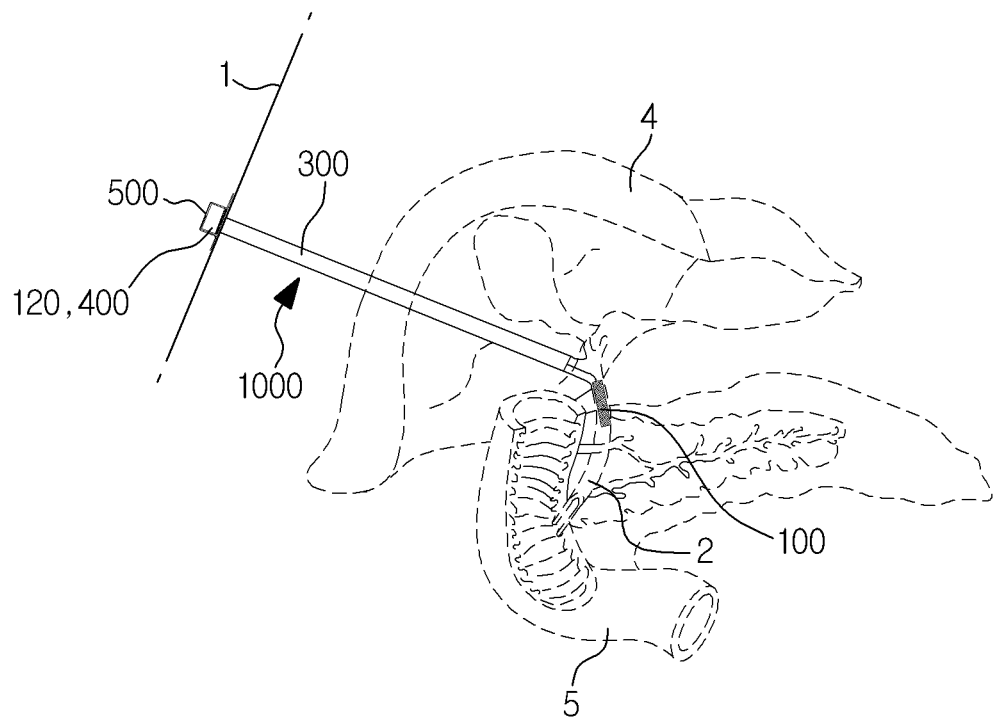

【FIG. 17】
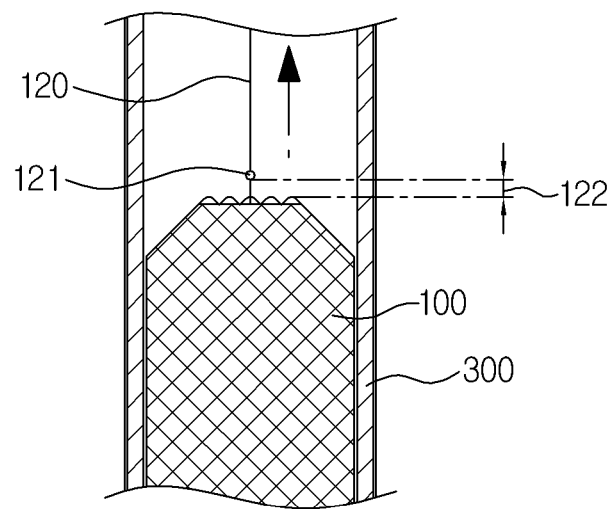
【FIG. 18】
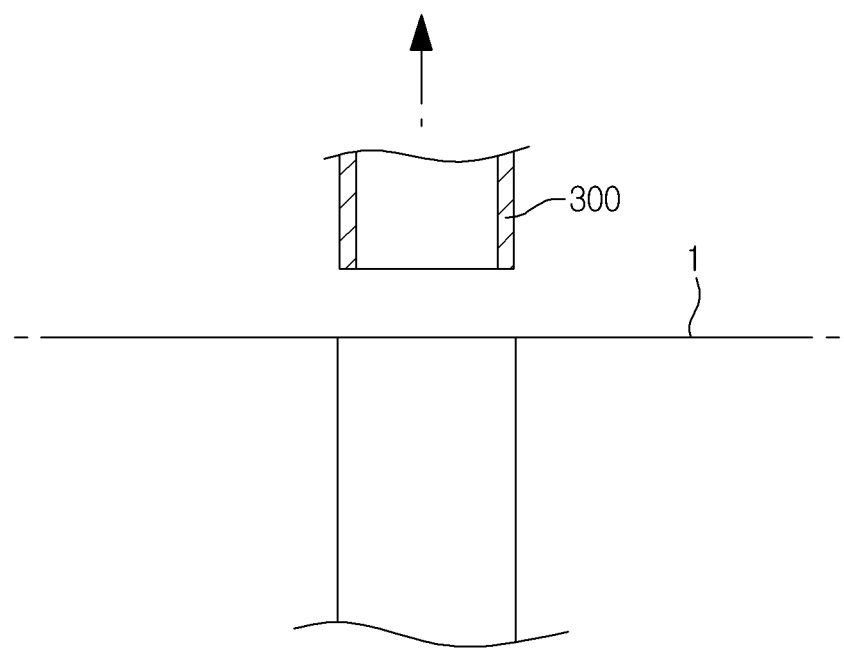

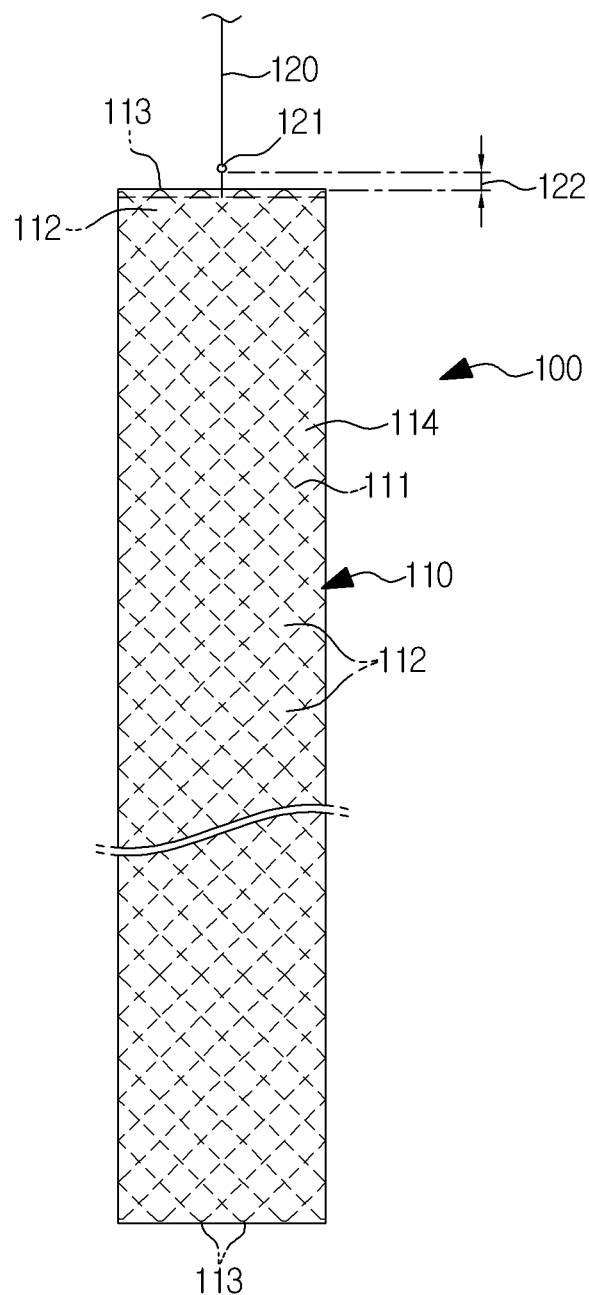
[FIG. 19]

[FIG. 20]
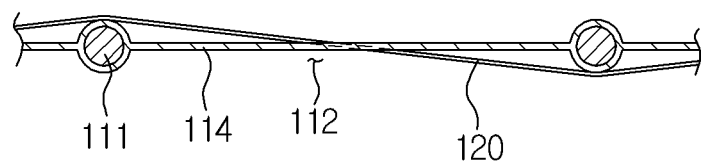

BILIARY STENT UNIT

CROSS REFERENCE TO RELATED APPLICATION

The present application claims priority to Korean Patent Application No. 10-2020-0124140, filed Sep. 24, 2020, the entire contents of which is incorporated herein for all purposes by this reference.

BACKGROUND OF THE INVENTION

Field of the Invention

The present disclosure relates to a biliary stent unit, particularly, to a biliary stent unit which prevents a stent from separating from a diseased part of the biliary tract due to shaking of a human body or an external force by a pulling string fixed outside the human body, that is, to the skin, and which reduces stimulus inside the human body due to shaking of the human body or an external force using a flexible soft tube protecting the pulling string.

Description of the Related Art

In general, stents have been used to expand the inside a lumen narrowed by a diseased part due to stricture or occlusion inside a human body so that the lumen is not narrowed back by the diseased part.

In relation to this subject, a biliary stent unit having a cylindrical body in which a space is formed by twisting or crossing in a zigzag pattern one or more pieces of shape memory ally wires together and several bending ends are circumferentially formed at both ends thereof has been disclosed in Patent Document 1. According to this configuration, a loop formed by tying both ends of a pulling string twisted in a circular band type in a zigzag pattern in the space of the cylindrical body is placed to be exposed lengthily outside a human body so that the stent does not slide in the biliary tract in surgery, and when the loop is pulled at the outside of the human body to remove the stent, the stent is taken out while the edge of the end of the stent closes toward the center, whereby the stent can be easily removed. Further, a port chamber is provided such that the loop of the pulling string passes through a tube-shaped catheter, which is inserted in a portion of a human body in which the stent is inserted, and is then tied and fixed in a port body extending from an end of the port catheter and configured to be positioned outside the human body. Accordingly, the loop is positioned inside the port catheter and is prevented from being contaminated.

However, according to Patent Document 1, since the port catheter is made of a hard material and is not flexible, stimulus inside a human body due to shaking of the body or an external force may be increased.

That is, the patient who has the biliary stent unit may feel pain.

DOCUMENTS OF RELATED ART (Patent Document 1) Korean Patent No. 10-1065365 (registered on Sep. 8, 2011)

SUMMARY OF THE INVENTION

Accordingly, an objective of the present disclosure is to provide a biliary stent unit which prevents a stent from separating from a diseased part of the biliary tract due to shaking of a human body or an external force by a pulling string fixed outside the human body, that is, to the skin, and which reduces stimulus inside the human body due to shaking of the human body or an external force using a flexible soft tube protecting the pulling string.

In order to achieve the objectives of the present disclosure, a biliary stent unit includes:

a stent having a cylindrical body, which has several spaces formed by twisting or crossing wires made of a superelastic shape memory alloy in a hollow cylindrical net shape and has several bending portions formed around an edge of both ends thereof, the stent including a pulling string being tied to a space of the several bending portions at a first end of the cylindrical body, the pulling string having two parts having different lengths and protruding from the first end of the cylindrical body, the pulling string having a knot formed by tying the two parts of the pulling string having different lengths such that a longer part of the two parts protrudes outside a human body, and the stent being applied to a diseased part generated due to stricture or occlusion in the biliary tract of the human body;

a pulling rod having a hook for fixing and releasing the longer part of the pulling string which is protruding outside the human body;

a soft tube in which the pulling string, which is fixed to the hook pulled out of the human body by pulling of the pulling rod, is inserted, the soft tube being guided close to the stent in the human body by the pulling string, and the soft tube having a male thread portion at a portion exposed outside the human body;

a cap having a female thread portion, which is fastened to the male thread portion, on an inner surface thereof, the cap having a through-hole on an outer surface thereof, through which the pulling string pulled out of the human body by pulling of the puling rod and then fixed to the hook passes, and the cap pressing and fixing the pulling string, which passes through the through-hole when the female thread portion and the male thread portion are fastened and is then wound on an outer surface of the applied soft tube, on the skin of the human body; and a fixing member covering the cap fixing the pulling string on the skin of the human body, thereby fixing the cap on the skin of the human body.

The present disclosure has an effect that the pulling string is fixed outside a human body, that is, on the skin of the human body by the cap coupled to the soft tube, and the cap is fixed outside the human body, that is, on the skin of the human body by the fixing member.

That is, there is an effect that since the pulling string is fixed on the skin of the human body, the stent is prevented from separating from a diseased part of the biliary tract due to shaking of the human body and an external force.

The present disclosure has an effect that stimulus that is generated in a human body due to shaking of the human body and an external force is reduced by the soft tube having flexibility and protecting the pulling string.

That is, there is an effect that a pain is prevented by the soft tube.

The present disclosure has an effect that since the cap is covered with the fixing member, the pulling string is not exposed outside.

That is, there is an effect that contamination of the pulling string due to exposure to the outside is prevented.

The present disclosure has an effect that the stent is guided through the soft tube and removed out of a human body when the pulling string is pulled after treatment for 2 to 16 weeks.

That is, there is an effect that the stent is easily removed out of a human body by the soft tube forming a passage, that is, a path in the human body.

There is an effect that the soft tube prevents the stent from being caught on organs inside a human body.

The present disclosure has an effect that it is possible to remove the stent by pulling only one part rather than both parts of the pulling string using the knot after treatment for 2 to 16 weeks.

The present disclosure has an effect that since the pulling string is fixed to the hook of the pulling rod, the pulling string is easily pulled out of a human body and is easily inserted into the soft tube.

The present disclosure has an effect that the soft tube prevents stricture of the pulling string and organs in a human body during treatment for 2 to 16 weeks.

The present disclosure has an effect that the gap between the stent and the knot prevents the compressed stent from being caught on the knot while the stent expands.

That is, there is an effect of preventing the biliary tract narrowed at a diseased part from failing to expand due to abnormal expansion of the stent.

The present disclosure has an effect that since there is a gap of 3 mm to 10 mm, the phenomenon that the compressed stent is caught on the knot when it expands and the phenomenon that the stent is caught when it is mounted on the stent delivery device are prevented.

That is, there is an effect that the stent is easily applied to a diseased part and is easily mounted on the stent delivery device.

Further, there is an effect that since the first end of the cylindrical body is closed well by the gap of 3 mm to 10 mm when the pulling string is pulled to remove the stent, the stent is not caught on the inlet of the soft tube.

That is, there is an effect that the stent is easily removed after treatment for 2 to 16 weeks.

The present disclosure has an effect that since contamination due to bacteria at the outside of a human body is prevented by the antibacterial agent coated on the pulling string, inflammation of the skin of a human body due to contamination is prevented.

The present disclosure has an effect that since the bile cannot permeate into the pulling string made of nylon, the bile is prevented from being discharged from the human body when the stent is removed.

The present disclosure has an effect that since the pulling string is a monofilament, there is no gap in which the bile permeates.

Further, there is an effect that the bile is prevented from being discharged from the human body when the stent is removed.

The present disclosure has an effect that since both parts of the pulling string are fastened to the loop and the knot is not untied when the pulling string is pulled, the pulling string is not separated from the stent when the pulling string is pulled.

That is, there is an effect that the stent is prevented from remaining without being removed in the biliary tract of a human body after treatment for 2 to 16 weeks.

The present disclosure has an effect that the membrane made of silicone or PTFE (Polytetrafluoroethylene) helps the bile move and prevents the bile from being stuck in the spaces.

Further, there is an effect that the bile is prevented from being discharged from the human body when the stent is removed.

BRIEF DESCRIPTION OF THE DRAWINGS

The above and other objectives, features and other advantages of the present invention will be more clearly understood from the following detailed description when taken in conjunction with the accompanying drawings, in which:

FIGS. 1 to 8 are views showing the configuration of a biliary stent unit according to an embodiment of the present disclosure;

FIGS. 9 to 18 are views showing an operated state of the biliary stent unit according to an embodiment of the present disclosure; and FIGS. 19 and 20 are front views showing a biliary stent unit according to another embodiment of the present disclosure.

DETAILED DESCRIPTION OF THE INVENTION

Hereafter, various embodiments of the present invention are described in detail with reference to the accompanying drawings.

As shown in FIGS. 1 to 20, a biliary stent unit 1000 according to various embodiments of the present disclosure is inserted in the biliary tract 2 between the liver 4 and the duodenum 5 inside a human body 1 to expand a diseased part 3 due to stricture or occlusion at the biliary tract 2 of the human body 1.

That is, the biliary stent unit 1000 is applied to a diseased part 3 that is generated at the biliary tract 2 of a human body 1 after hepatectomy and liver transplant due to hepatoma and cirrhosis, or a diseased part 3 that is generated at the biliary tract 2 of the human body 1 due to bile duct cancer.

The biliary stent unit 1000 is maintained at the operated position for 2 to 16 weeks until the diseased part 3 is completely cured.

As shown in FIGS. 1 to 18, the biliary stent unit 1000 according to an embodiment of the present disclosure includes a stent 100 that is applied to a diseased part 3 generated at the biliary tract 2 of the human body 1 due to stricture or occlusion by a stent delivery device.

The stent 100 includes a cylindrical body 110 that has several spaces 112 formed by twisting or crossing one or more wires 111, which are made of a superelastic shape memory alloy, in a hollow cylindrical net shape, and that has several bending portions 113 formed around the edge of both ends thereof.

The cylindrical body 100 of the stent 100 is compressed in a stent delivery device, and is separated and expanded from the stent delivery device when it is applied to a diseased part 3 by the stent delivery device.

The stent 100 includes a pulling string 120 that is fastened to a space 112 of the several bending portions 113 at a first end of the cylindrical body 110, that has two parts having different lengths and protruding from the first end of the cylindrical body 110, that has a knot 121 formed by tying the two parts having different lengths, and of which the longer part protrudes outside the human body 1.

The cylindrical body 110 of the stent 100 is mounted in the stent delivery device such that the pulling string 120 is positioned in the opposite direction to the direction that passes through the skin, liver 4, and biliary tract 2 of the human body 1.

The pulling string 120 is coated with an antibacterial agent, so an antibacterial agent layer 120a is formed on the outer surface thereof.

The pulling string 120 is made of nylon.

The pulling string 120 is a monofilament not formed by twisting several pieces of strings.

There is a gap 122 between the knot 121 and the first end of the cylindrical body 110 at which the pulling string 120 is fastened to the space 112 of the several bending portion 113.

When the gap 122 is 3 mm or less, the first end of the cylindrical body 110 and the knot 121 are too close to each other, so the compressed stent 110 may not normally expand by being blocked by the knot 121 while expanding for surgery.

When the gap 122 is 10 mm or more, the first end of the cylindrical body 110 and the knot 121 are too far from each other, so the first end of the cylindrical body 110 may not normally close when the pulling string 120 is pulled to remove the stent 100.

Further, when the gap 122 is 10 mm or more, the first end of the cylindrical body 110 and the knot 121 are too far from each other, so the knot 121 is frequently stuck in a stent delivery device when the stent 100 is mounted in the stent delivery device, and accordingly, it is difficult to mount the stent 100.

Accordingly, the gap 122 is set as 3 mm to 10 mm.

As shown in FIGS. 2 to 4, the knot 121 is formed by: bringing a first part 121a of the pulling string 120, which protrudes from the first end of the cylindrical body 110, and a second part 121b of the pulling string 120, which protrudes from the first end of the cylindrical body 110 shorter than the first part 121a of the pulling string 120, into contact with each other; forming a loop 121c by twisting the first part 121a and the second part 121b of the pulling string 120; passing the first part 121a and the second part 121b of the pulling string 120 left after forming the loop 121c through the loop 121c; and then pulling the first part 121a and the second part 121b of the pulling string 120 that have passed through the loop 121c such that the first part 121a and the second part 121b of the pulling string 120 are fastened while the loop 121c is constricted.

That is, the knot 121 is formed not to be untied when the pulling string 120 is pulled.

The first part 121a of the pulling string 120 protrudes outside the human body 1.

The biliary stent unit 1000 includes a pulling rod 200 having a hook 210 for fixing and releasing the pulling string 120 protruding outside the human body 1.

The pulling rod 200 is formed like a long iron core.

The pulling string 120 may be wound on the hook 210 or may have a loop in which the hook 210 is inserted to be hooked and fixed to the hook 210.

The biliary stent unit 1000 includes a soft tube 300 in which the pulling string 120, which is fixed to the hook 210 and is pulled out of the human body 1 by pulling of the pulling rod 200, is inserted, that is guided close to the stent 100 in the human body 1 by the pulling string 120, and that has a male thread portion 310 at a portion exposed outside the human body 1.

The soft tube 300 is formed similar to a duct and is made of silicone or rubber.

The biliary stent unit 1000 includes a cap 400 that has a female thread portion 410, which is fastened to the male thread portion 310, on the inner surface thereof, that has a through-hole 420 on the outer surface thereof, through which the pulling string 120 pulled out of the human body 1 by pulling of the puling rod 200 and then released from the hook 210 passes, and that presses and fixes the pulling string 120, which passes through the through-hole 420 when the female thread portion 410 and the male thread portion 310 are fastened and is then wound on the outer surface of the implanted soft tube 300, on the skin of the human body 1.

The cap 400 is made of silicone or rubber.

The biliary stent unit 1000 includes a fixing member 500 that covers the cap 400 fixing the pulling string 120 on the skin of the human body 1, thereby fixing the cap 400 on the skin of the human body 1.

The fixing member 500 includes a gauze or a bandage covering the cap 400 fixing the pulling string 120 on the skin of the human body 1, an adhesive or a tape attaching the gauze or the bandage to the skin of the human body 1, etc.

As shown in FIGS. 19 and 20, the stent 100 of the biliary stent unit 1000 according to another embodiment of the present disclosure includes has a membrane 114 made of silicone or PTFE (Polytetrafluoroethylene) on the cylindrical body 110.

The spaces 112 are covered with the membrane 114.

The pulling string 120 is fastened to the space 112 of the bending portions 113 and the membrane 114.

The operation of the biliary stent unit 1000 having the above configuration of the present disclosure is described hereafter.

As shown in FIGS. 1 to 18, the biliary stent unit 1000 according to an embodiment of the present disclosure is applied to a diseased part 3 generated at the biliary tract 2 of the human body 1 due to stricture or occlusion.

In detail, an operator cuts the skin of the human body 1, secures a visual field using an endoscope, inserts a stent delivery device equipped with the stent 100 through the skin, the liver 4, and the biliary tract 2 of the human body 1, checks the position of a diseased part 3 using the endoscope, and applies the stent 100 to the diseased part 3 using the stent delivery device, thereby expanding the diseased part 3.

Since there is a gap 122 of 3 mm to 10 mm between the knot 121 and the first end of the cylindrical body 110 of the stent 100, the compressed stent 100 easily expands in the diseased part 3 without being caught on the knot 121.

The diseased part 3 is inserted in the spaces 112 of the stent 100.

When the stent delivery device is removed from the human body 1, the pulling string 120 is protruded out of the human body 1 by the stent delivery device.

That is, the longer part 121a of the pulling string 120 which protrudes from the first end of the cylindrical body 110 protrudes out of the human body 1.

Next, the pulling string 120 protruding out of the human body 1 is fixed to the hook 210 of the pulling rod 200 and then the pulling rod 200 is pulled, whereby the pulling string 120 fixed to the hook 210 is pulled out of the human body 1.

Further, the pulling string 120 fixed to the hook 210 is inserted into the soft tube 300.

The pulling string 120 is released from the hook 210 pulled out of the soft tube 300 and then the soft tube 300 is moved along the pulling string 120 and inserted into the skin, the liver 4, and the biliary tract 2 of the human body 1 pierced by the stent delivery device.

That is, the soft tube 300 is guided by the pulling string 120 and positioned in the skin, liver 4, and biliary tract 2 of the human body 1 pierced by the stent delivery device.

The soft tube 300 is left close to the stent 100 in the human body 1.

The soft tube 300 provides a passage, that is, a path for easily removing the stent 100 after treatment for 2 to 16 weeks in the human body 1.

The pulling string 120 released from the hook 210 is inserted through the through-hole 420 of the cap 400 and then wound on the outer surface on the portion of the soft tube 300 exposed outside the human body 1.

Next, the male thread portion 310 of the soft tube 300 exposed outside the human body 1 and the female thread portion 410 of the cap 400 are fastened to each other, whereby the pulling string 120 wound on the outer surface of the soft tube 300 is pressed by the cap 400.

Accordingly, the pulling string 120 is pressed on the cap 400 and fixed on the skin of the human body 1.

The cap 400 fixing the pulling string 120 on the skin of the human body 1 is covered with the fixing member 500, whereby the cap 400 is fixed on the skin of the human body 1.

Accordingly, the pulling string 120 is fixed at the outside of the human body 1, that is, fixed on the skin, and the stent 100 is fixed in the human body 1, that is, in the diseased part 3 of the biliary tract 2.

Therefore, the stent 100 of the biliary stent unit 1000 according to an embodiment of the present disclosure is prevented from separating from the diseased part 3 due to shaking of the human body and an external force.

The soft tube 300 is deformed when the human body 1 is shaken and an external force is applied, and is returned to the initial state by elasticity when shaking of the human body 1 and the external force are removed.

Since the antibacterial agent layer 120a is formed on the outer surface of the pulling string 120, contamination of the pulling string 120 due to bacteria when the pulling string 120 is exposed outside the human body 1 for a long period of time is prevented.

Since the pulling string 120 is made of nylon, the bile flowing through the biliary tract 2 is prevented from permeating into the pulling string 120.

When the diseased part 3 is completely cured for 2 to 16 weeks, the biliary stent unit 1000 is removed.

In detail, the fixing member 500 is removed from the cap 400 on the skin of the human body 1, and then the female thread portion 410 of the cap 400 and the male thread portion 310 of the soft tube 300 are separated.

In this process, the pressure applied to the pulling string 120 by the cap 400 is removed.

Thereafter, the pulling string 120 is pulled.

As the pulling string 120 is pulled, the cylindrical body 110 is inserted into the soft tube 300 while the first end to which the pulling string 120 is fastened is closed.

The first end of the cylindrical body 110 to which the pulling string 120 is fastened is closed well by the gap 122 of 3 mm to 10 mm, so the stent 100 is easily inserted into the soft tube 300 when the pulling string 120 is pulled.

Accordingly, the stent 100 is taken out of the biliary tract 2 of the human body 1.

Since both parts 121a and 121b of the pulling string 120 are fastened to the loop 121c, the knot 121 is not untied when the pulling string 120 is pulled.

When the pulling string 120 is pulled, the stent 100 is guided by the soft tube 300 and taken out of the soft tube 300.

That is, the stent 100 is easily guided through the soft tube 300 forming a passage, that is, a path in the human body 1 and taken out of the soft tube 300, thereby being removed.

Then, the soft tube 300 is pulled out of the human body 1.

As shown in FIGS. 19 and 20, the bile flowing through the biliary tract 2 is easily guided to the duodenum 5 by of membrane 114 made silicone or PTFE the (Polytetrafluoroethylene) of the stent 100 of the biliary stent unit 1000 according to another embodiment of the present disclosure.

The diseased part 3 is not inserted in the spaces 112 covered by the membrane 114.

Although the present disclosure was described above with reference to specific embodiments, the present disclosure is not limited to the embodiments and may be changed and modified in various ways by those skilled in the art without departing from the scope of the present disclosure.

What is claimed is:

1. A biliary stent unit comprising:
a stent having a cylindrical body, which has several spaces formed by twisting or crossing wires made of a superelastic shape memory alloy in a hollow cylindrical net shape and having several bending portions formed around an edge of both ends thereof, the stent including a pulling string tied to a space of the several bending portions at a first end of the cylindrical body, the pulling string having two parts having different lengths and protruding from the first end of the cylindrical body, the pulling string having a knot formed by tying the two parts of the pulling string having different lengths such that a longer part of the two parts protrudes outside a human body, and the stent being applied to a diseased part generated due to stricture or occlusion in the biliary tract of the human body;
a pulling rod having a hook for fixing and releasing the longer part of the pulling string which is protruding outside the human body;
the pulling string is fixed to the hook when the pulling rod is pulled out of the human body;
a soft tube in which the pulling string is inserted, the soft tube being guided close to the stent in the human body by the pulling string, and the soft tube having a male thread portion at a portion exposed outside the human body;
a cap having a female thread portion, which is fastened to the male thread portion, on an inner surface thereof, the cap having a through-hole on an outer surface thereof through which the pulling string passes, and the cap pressing and fixing the pulling string, the pulling string is then wound on an outer surface of the applied soft tube, on the skin of the human body; and
a fixing member covering the cap, and fixing the pulling string on the skin of the human body, thereby fixing the cap on the skin of the human body.

2. The biliary stent unit of claim 1, wherein the stent has a membrane made of silicone or PTFE (Polytetrafluoroethylene) on the cylindrical body to cover the spaces, and
the pulling string is fastened to the space of the bending portions and the membrane.

3. The biliary stent unit of claim 1, wherein a gap is formed between the knot and the first end of the cylindrical body at which the pulling string is fastened to the space of the several bending portions.

4. The biliary stent unit of claim 3, wherein the gap is 3 mm to 10 mm.

5. The stent unit of claim 1, wherein the pulling string is coated with an antibacterial agent.

6. The biliary stent unit of claim 1, wherein the pulling string is made of nylon.

7. The biliary stent unit of claim 1, wherein the pulling string is a monofilament.

8. The biliary stent unit of claim 1, wherein the knot is formed by:
- bringing a first part of the pulling string, which protrudes from the first end of the cylindrical body, and a second part of the pulling string, which protrudes from the first end of the cylindrical body shorter than the first part of the pulling string, into contact with each other;
- forming a loop by twisting the first part and the second part of the pulling string;
- passing the first part and the second part of the pulling string remaining after forming the loop through the loop; and
- pulling the first part and the second part of the pulling string that have passed through the loop such that the first part and the second part of the pulling string are fastened while the loop is constricted.

\* \* \* \* \*